(12) United States Patent
Scheiner et al.

(10) Patent No.: US 6,912,420 B2
(45) Date of Patent: Jun. 28, 2005

(54) CARDIAC RHYTHM MANAGEMENT SYSTEM FOR HYPOTENSION

(75) Inventors: Avram Scheiner, Vadnais Heights, MN (US); Douglas R. Daum, Oakdale, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 128 days.

(21) Appl. No.: 09/832,365

(22) Filed: Apr. 10, 2001

(65) Prior Publication Data

US 2002/0147475 A1 Oct. 10, 2002

(51) Int. Cl.⁷ .................................................. A61N 1/08
(52) U.S. Cl. ....................................................... 607/17
(58) Field of Search .............................. 600/485, 504, 600/505, 506, 509, 513, 547; 607/4, 5, 6, 7, 8, 9, 28, 42, 119, 117

(56) References Cited

U.S. PATENT DOCUMENTS

| | | | |
|---|---|---|---|
| 3,340,867 A | 9/1967 | Kubicek et al. | |
| 3,871,359 A | 3/1975 | Pacela | |
| 4,003,379 A | 1/1977 | Ellinwood, Jr. | 128/260 |
| RE30,101 E | 9/1979 | Kubicek et al. | |
| 4,271,192 A | 6/1981 | Wurtman et al. | 424/319 |
| 4,437,469 A | 3/1984 | Djordjevich et al. | |
| 4,450,527 A | 5/1984 | Sramek | |
| 4,470,987 A | 9/1984 | Wurtman et al. | 424/259 |
| 4,472,420 A | 9/1984 | Toth | |
| 4,472,431 A | 9/1984 | Toth | |
| 4,576,183 A | 3/1986 | Plicchi et al. | 600/536 |
| 4,651,716 A | 3/1987 | Forester et al. | 128/1 D |
| 4,884,576 A | 12/1989 | Alt | 128/419 PG |
| 4,919,136 A | 4/1990 | Alt | |
| 4,987,897 A | 1/1991 | Funke | 128/419 PG |
| 5,025,786 A | 6/1991 | Siegel | 600/375 |
| 5,031,629 A | 7/1991 | DeMarzo | |
| 5,113,869 A | 5/1992 | Nappholz et al. | 128/696 |
| 5,117,825 A | 6/1992 | Grevious | 128/419 PG |
| 5,178,154 A | 1/1993 | Ackmann et al. | |
| 5,199,428 A | 4/1993 | Obel et al. | 128/419 C |
| 5,213,098 A | 5/1993 | Bennett et al. | 128/419 |

(Continued)

FOREIGN PATENT DOCUMENTS

| | | | |
|---|---|---|---|
| EP | 348271 | 12/1989 | |
| EP | 0 620 420 A1 * | 1/1994 | G01F/1/56 |

(Continued)

OTHER PUBLICATIONS

Luepker, R. V., et al., "Transthoracic Electrical Impedance: Quantitative Evaluation of a Non–Invasive Measure of Thoracic Fluid Volume", *American Heart Journal*, vol. 85, No. 1, (Jan. 1973),83–93.

(Continued)

*Primary Examiner*—Jeffrey R. Jastrzab
*Assistant Examiner*—Frances P. Oropeza
(74) *Attorney, Agent, or Firm*—Schwegman, Lundberg, Woessner & Kluth, P.A.

(57) ABSTRACT

A cardiac rhythm management system detects hypotension based on a measurement of thoracic impedance. It also provides therapy to treat the hypotension.

34 Claims, 10 Drawing Sheets

U.S. PATENT DOCUMENTS

| | | | |
|---|---|---|---|
| 5,233,985 A | 8/1993 | Hudrlik | 607/27 |
| 5,246,008 A | 9/1993 | Mueller et al. | 600/508 |
| 5,271,395 A | 12/1993 | Wahlstrand et al. | 607/9 |
| 5,282,840 A * | 2/1994 | Hudrlik | 607/28 |
| 5,284,136 A | 2/1994 | Hauck et al. | |
| 5,292,343 A | 3/1994 | Blanchette et al. | 607/32 |
| 5,300,093 A | 4/1994 | Koestner et al. | 607/32 |
| 5,309,917 A | 5/1994 | Wang et al. | |
| 5,313,953 A | 5/1994 | Yomtov et al. | 128/696 |
| 5,324,309 A | 6/1994 | Kallok | 607/5 |
| 5,324,315 A | 6/1994 | Grevious | 607/60 |
| 5,344,429 A | 9/1994 | Smits | 607/5 |
| 5,354,317 A | 10/1994 | Alt | 607/19 |
| 5,354,319 A | 10/1994 | Wyborny et al. | 128/904 |
| 5,370,665 A | 12/1994 | Hudrlik | 607/9 |
| 5,411,031 A | 5/1995 | Yomtov | 128/706 |
| 5,441,525 A | 8/1995 | Shelton et al. | 607/23 |
| 5,443,073 A | 8/1995 | Wang et al. | |
| 5,464,434 A | 11/1995 | Alt | 607/6 |
| 5,479,369 A | 12/1995 | Matsumura et al. | 365/189.05 |
| 5,501,701 A | 3/1996 | Markowitz et al. | 607/9 |
| 5,505,209 A | 4/1996 | Reining | |
| 5,507,785 A | 4/1996 | Deno | 607/24 |
| 5,526,808 A | 6/1996 | Kaminsky | |
| 5,534,018 A | 7/1996 | Wahlstrand et al. | 607/27 |
| 5,540,728 A | 7/1996 | Shelton et al. | 607/23 |
| 5,562,711 A * | 10/1996 | Yerich et al. | 607/17 |
| 5,626,623 A | 5/1997 | Kieval et al. | 607/23 |
| 5,642,734 A | 7/1997 | Ruben et al. | |
| 5,676,686 A | 10/1997 | Jensen et al. | 607/9 |
| 5,685,316 A | 11/1997 | Schookin et al. | |
| 5,706,829 A | 1/1998 | Kadri | 128/898 |
| 5,725,561 A | 3/1998 | Stroebel et al. | 607/9 |
| 5,725,562 A | 3/1998 | Sheldon | 607/19 |
| 5,732,710 A | 3/1998 | Rabinovich et al. | 600/547 |
| 5,749,369 A | 5/1998 | Rabinovich et al. | 600/547 |
| 5,749,900 A | 5/1998 | Schroeppel et al. | 607/4 |
| 5,782,774 A | 7/1998 | Shmulewitz | |
| 5,782,884 A | 7/1998 | Stotts et al. | |
| 5,788,643 A | 8/1998 | Feldman | 600/506 |
| 5,791,349 A | 8/1998 | Shmulewitz | |
| 5,800,464 A | 9/1998 | Kieval | 607/9 |
| 5,865,760 A | 2/1999 | Lidman et al. | |
| 5,874,420 A | 2/1999 | Pelleg | 514/81 |
| 5,876,353 A | 3/1999 | Riff | 600/547 |
| 5,913,879 A * | 6/1999 | Ferek-Petric et al. | 607/14 |
| 5,919,210 A | 7/1999 | Lurie et al. | 607/3 |
| 5,957,861 A * | 9/1999 | Combs et al. | 600/547 |
| 5,957,957 A | 9/1999 | Sheldon | 600/17 |
| 6,035,233 A | 3/2000 | Schroeppel et al. | 600/515 |
| 6,044,297 A * | 3/2000 | Sheldon et al. | 607/17 |
| 6,049,735 A | 4/2000 | Hartley et al. | 607/9 |
| 6,075,015 A | 6/2000 | Sestelo et al. | |
| 6,076,015 A | 6/2000 | Hartley et al. | 607/20 |
| 6,078,834 A | 6/2000 | Lurie et al. | 607/3 |
| 6,095,987 A | 8/2000 | Shmulewitz et al. | |
| 6,104,949 A * | 8/2000 | Pitts Crick et al. | 600/547 |
| 6,161,038 A | 12/2000 | Schookin et al. | |
| 6,186,955 B1 | 2/2001 | Baura | |
| 6,228,033 B1 | 5/2001 | Koobi et al. | |
| 6,292,689 B1 | 9/2001 | Wallace et al. | |
| 6,317,631 B1 | 11/2001 | Ben-Haim et al. | 607/9 |
| 6,438,408 B1 | 8/2002 | Mulligan et al. | |
| 6,473,640 B1 * | 10/2002 | Erlebacher | 600/547 |
| 6,511,438 B2 | 1/2003 | Bernstein et al. | |
| 6,512,949 B1 | 1/2003 | Combs et al. | 600/547 |
| 6,560,481 B1 | 5/2003 | Heethaar et al. | |
| 6,561,986 B2 | 5/2003 | Baura et al. | |
| 6,602,201 B1 | 8/2003 | Hepp | |
| 6,625,492 B2 | 9/2003 | Florio et al. | 607/17 |
| 6,636,754 B1 | 10/2003 | Baura et al. | |
| 6,748,271 B2 | 6/2004 | Spinelli et al. | |
| 2002/0138014 A1 | 9/2002 | Baura et al. | |
| 2002/0147476 A1 | 10/2002 | Daum | 607/17 |
| 2002/0193689 A1 | 12/2002 | Bernstein et al. | |
| 2003/0023279 A1 | 1/2003 | Spinelli et al. | 607/9 |
| 2003/0028221 A1 | 2/2003 | Zhu et al. | 607/9 |
| 2003/0074029 A1 | 4/2003 | Deno et al. | |
| 2003/0191503 A1 | 10/2003 | Zhu et al. | 607/17 |
| 2004/0049235 A1 | 3/2004 | Deno et al. | |

FOREIGN PATENT DOCUMENTS

| | | | |
|---|---|---|---|
| EP | 0620420 | 10/1994 | G01F/1/56 |
| EP | 1057498 | 12/2000 | |
| EP | 1078597 | 2/2001 | |
| EP | 606301 | 12/2001 | |
| EP | 1247487 | 10/2002 | |
| EP | 1275342 | 1/2003 | |
| EP | 771172 | 4/2003 | |
| WO | WO-8400227 | 1/1984 | |
| WO | WO-9304627 | 3/1993 | |
| WO | WO-9601586 | 1/1996 | |
| WO | WO-9737591 | 10/1997 | |
| WO | WO-9738628 | 10/1997 | |
| WO | WO-9851211 | 11/1998 | |
| WO | WO-0141638 | 6/2001 | |
| WO | WO-02053026 | 7/2002 | |
| WO | WO-02053228 | 7/2002 | |
| WO | WO-03020364 | 3/2003 | |

OTHER PUBLICATIONS

Mai, J., et al., "Enhanced Rate Response Algorithm for Orthostatic Compensation Pacing" *Pace*, 23, NASPE Abstracts, Abstract No. 678, p. 722, (Apr. 2000).

Berman, I R., et al., "Transthoracic electrical impedance s a guide to intravascular overload", *Arch Surg.*, 102(1), (Jan. 1971),61–4.

Charach, Gideon, et al., "Transthoracic monitoring of the impedance of the right lung in patients with cardiogenic pulmonary edema", *Crit Care Med.*, 29(6), (Jun. 2001), 1137–44.

Ellenbogen, Kenneth A., et al., "Clinical cardiac pacing", *Philadelphia : Saunders*, (1995),219–233.

Kusumoto, F M., et al., "Medical Progress: Cardiac Pacing", *New England Journal of Medicine,* 334(2), (Jan. 11, 1996), 89–98.

Lau, C P., et al., "Rate–responsive pacing with a pacemaker that detects respiratory rate (Biorate): clinical advantages and complications", *Clin Cardiol.*, 11(5), (May 1988), 318–24.

Pomerantz, M, et al., "Transthoracic electrical impedance for the early detection of pulmonary edema", *Surgery,* 66(1), (Jul. 1969),260–8.

Shoemaker, W C., et al., "Multicenter trial of a new thoracic electrical bioimpedance device for cardiac output estimation", *Crit Care Med.*, 22(12), (Dec. 1994),1907–12.

Viirola, H , "Controlled growth of antimony–doped tin dioxide thin films by atomic layer epitaxy", *Thin Solid Films,* 251, (Nov. 1994),127–135.

Viirola, H , "Controlled growth of tin oxide thin films by atomic layer epitaxy", *Thin Solid Films,* 249(2), (Sep. 1994), 144–149.

Visokay, M R., "Application of HfSiON as a gate dielectric material", *Applied Physics Letters, 80(17)*, (Apr. 2002), 3183–3185.

Wuerz, Richard C., et al., "Effects of prehospital medications on mortality and length of stay in congestive heart failure", *Annals of Emergency Medicine, 21(6)*, (Jun. 1992), 669–74.

Yu, Cheuk–Man, et al., "Early warning of CHF hospitalization by intra–thoracic impedance measurement in CHF patients with pacemakers", *Pacing and Clinical Electrophysiology, 24*, (Apr. 2001),19.

Ebert, T J., et al., "The use of thoracic impedance for determining thoracic blood volume changes in man", *Aviat Space Environ Med., 57(1)*, (Jan. 1986),49–53.

Petersen, M E., et al., "Cardiac pacing for vasovagal syncope: a reasonable therapeutic option?", *Pacing Clin Electrophysiol., 20(3 Pt 2)*, (Mar. 1997),824–6.

Spinelli, J. C., "Method and System for Treatment of Neurocardiogenic Syncore", *U.S. Appl. No. 10/862,631, filed Jun. 7, 2004*, 15 pages.

Sra, J S., et al., "Cardiac pacing during neurocardiogenic (vasovagal) syncope", *J Cardiovasc Electrophysiol., 6(9)*, (Sep. 1995),751–60.

Stahmann, Jeffrey, "Thoracic Impedance Detection with Blood Resistivity Compensation", *U.S. Appl. No. 10/921, 503, Filed Aug. 19, 2004*, 38 pgs.

\* cited by examiner

CARDIAC RHYTHM MANAGEMENT SYSTEM FOR HYPOTENSION

TECHNICAL FIELD

The present system relates generally to cardiac rhythm management systems and particularly, but not by way of limitation, to a such a system for hypotension.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers coordinate atrial and ventricular contractions to improve pumping efficiency. Cardiac rhythm management systems also include coordination devices for coordinating the contractions of both the right and left sides of the heart for improved pumping efficiency.

Cardiac rhythm management systems also include defibrillators that are capable of delivering higher energy electrical stimuli to the heart. Such defibrillators also include cardioverters, which synchronize the delivery of such stimuli to portions of sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by some patients is hypotension, that is, low blood pressure. Hypotension can result in dizziness, sometimes referred to as presyncope. Hypotension can even lead to unconsciousness, sometimes referred to as syncope. One cause of hypotension is an excess shifting of blood in the circulatory system toward the extremities (arms and legs) and away from vital organs in the patient's head and thorax. This can occur, for example, when the patient changes posture from lying horizontal or sitting with legs elevated to a position in which the patient is sitting or standing erect. Hypotension resulting from such changes in posture is referred to herein as orthostatic hypotension. However, hypotension may also have causes other than changes in posture. For example, maintaining the same posture for an extended period of time (e.g., sitting erect during an intercontinental airplane flight) may also cause hypotension. Moreover, certain cardiovascular disorders may result in hypotension independent of postural changes, or may exacerbate orthostatic hypotension.

For example, disautonomic syncope is a problem with the autonomic nervous system. In normal patients, the autonomic nervous system constricts the blood vessels in the extremities in response to a change to a more upright posture. This venoconstriction of the blood vessels in the extremities reduces the amount of blood that would otherwise shift to the extremities when the patient changes to a more upright posture. In some patients, however, this response by the autonomic nervous system is absent, or is even reversed by a venodilation of blood vessels in the extremities. Such patients are likely to experience hypotension. Moreover, this deficient response by the autonomic nervous system may occur even without changes in posture, leading to hypotension that is not necessarily orthostatic in nature.

Another example of a cardiovascular cause of hypotension is vasovagal syncope. In normal patients, a change to a more upright posture results in an increased heart rate. For example, for a patient that is at rest, the heart rate may temporarily increase from 60 beats per minute (bpm) to 80 bpm when the patient stands up after laying horizontally. In some patients, however, this autonomic response is absent-resulting in a drop in heart rate. This may also lead to hypotension as blood shifts away from the head and thorax into the extremities. Regardless of the cause of hypotension, the resulting symptoms of dizziness or loss of consciousness may be extremely dangerous. This is particularly so for elderly patients who are at increased risk of injury from a fall resulting from the dizziness or loss of consciousness. Hypotension is also an obvious danger for persons operating motor vehicles or other machinery. For these and other reasons, there is a need to treat hypotension to avoid these symptoms and associated risks.

SUMMARY OF THE INVENTION

This document discusses, among other things, a cardiac rhythm management system using thoracic impedance measurements to detect and treat hypotension. In one embodiment, the system receives a thoracic impedance signal. An averager or other lowpass filter obtains a baseline portion of the thoracic impedance signal that is associated with a fluid shift away from the thorax. A rate of pacing therapy is increased in response to the detected fluid shift away from the thorax to treat the hypotension. Several other therapies are also discussed. Other aspects of the invention will be apparent on reading the following detailed description of the invention and viewing the drawings that form a part thereof.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components.

DETAILED DESCRIPTION

Figure 1:
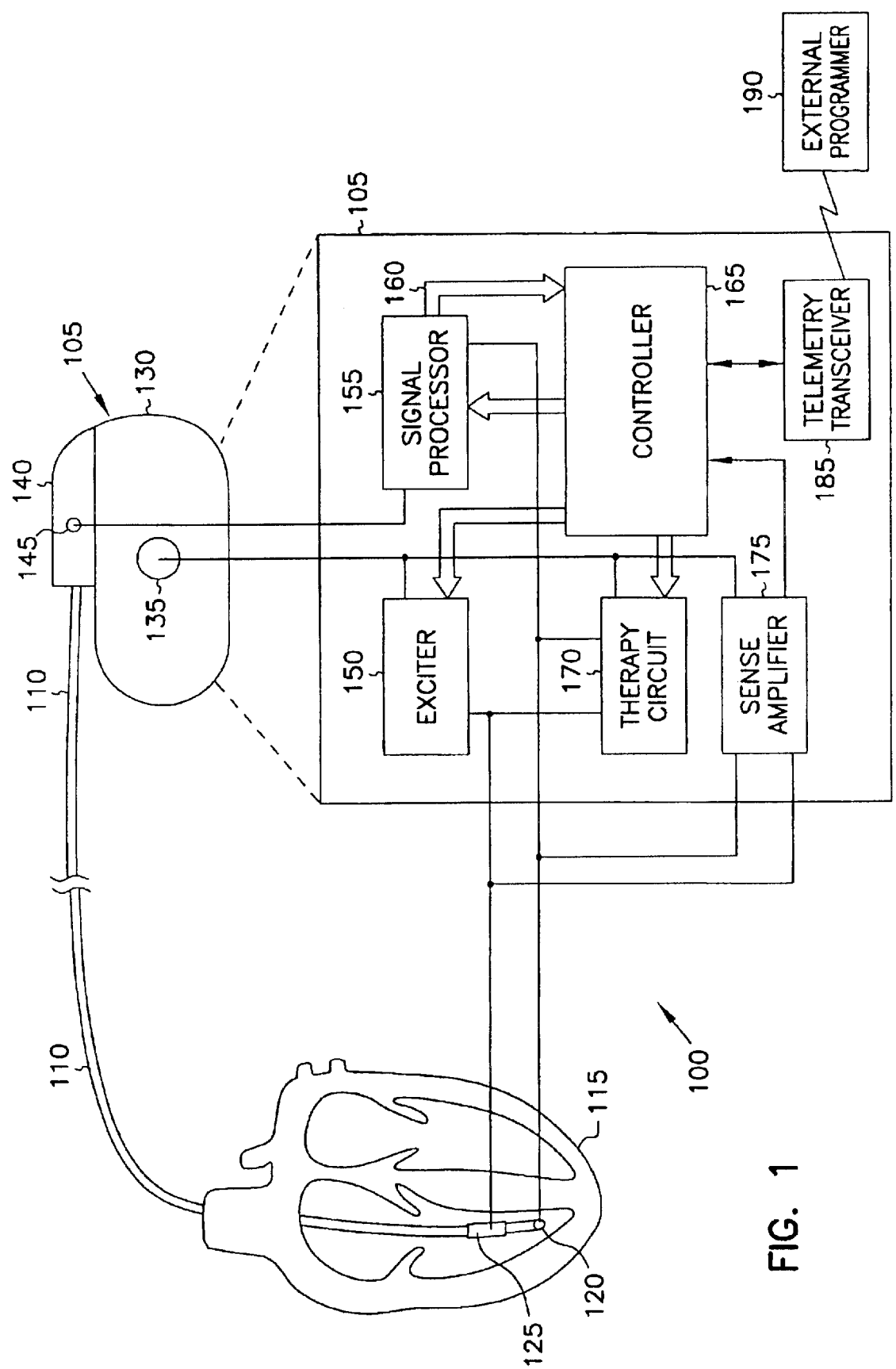
FIG. 1 is a schematic/block diagram illustrating generally one embodiment of portions of a cardiac rhythm management system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components. The term "and/or" refers to a nonexclusive "or" (i.e., "A and/or B" includes both "A and B" as well as "A or B").

The present methods and apparatus will be discussed in applications involving implantable medical devices including, but not limited to, implantable cardiac rhythm management systems such as pacemakers, cardioverter/defibrillators, pacer/defibrillators, and biventricular or other multi-site coordination devices. However, it is understood that the present methods and apparatus may be employed in unimplanted devices, including, but not limited to, external pacemakers, cardioverter/defibrillators, pacer/defibrillators, biventricular or other multi-site coordination devices, monitors, programmers and recorders.

This document discusses a cardiac rhythm management system that detects hypotension by measuring an impedance across a portion of a patient's thorax, referred to as "transthoracic impedance" or simply abbreviated as "thoracic impedance." In this document, the term thorax is understood to include the portion of the subject's body other than the head, arms, and legs. The system provides appropriate responsive therapy, such as by adjusting the rate of delivery of pacing stimuli to the heart to help avoid symptoms associated with hypotension, such as dizziness or fainting.

Electrode Configuration and Top-Level Block Diagram

FIG. 1 is a schematic/block diagram illustrating generally, by way of example, but not by way of limitation, one embodiment of a cardiac rhythm management system 100 according to the present invention. In this embodiment, system 100 includes, among other things, cardiac rhythm management device 105 and leadwire ("lead") 110 for communicating signals between device 105 and a portion of a living organism, such as heart 115. Embodiments of device 105 include, among other things, bradycardia and antitachycardia pacemakers, cardioverters, defibrillators, combination pacemaker/defibrillators, drug delivery devices, and any other implantable or external cardiac rhythm management apparatus capable of providing therapy to heart 115. System 100 may also include additional components such as, for example, a remote programmer 190 capable of communicating with device 105 via a transmitter or receiver, such as telemetry transceiver 185.

In one embodiment, portions of system 100 (e.g., device 105) are implantable in the living organism, such as in a pectoral or abdominal region of a human patient, or elsewhere. In another embodiment, portions of system 100 (e.g., device 105) are alternatively disposed externally to the human patient. In the illustrated embodiment, portions of lead 110 are disposed in the right ventricle, however, any other positioning of lead 110 is included within the present invention. For example, lead 110 may alternatively be positioned in a location that is associated with the right atrium and/or superior vena cava, the coronary sinus or great cardiac vein, the left atrium or ventricle, epicardially, or elsewhere. In one embodiment, lead 110 is a commercially available bipolar pacing lead. System 100 can also include other leads in addition to or instead of lead 110, appropriately disposed, such as in or around heart 115, or elsewhere. In one external embodiment, lead 110 is disposed external to the patient and includes external skin electrodes that are associated with the heart and/or thorax.

In one embodiment, system 100 includes at least four electrodes, such as discussed in Hauck et al. U.S. Pat. No. 5,284,136 entitled "DUAL INDIFFERENT ELECTRODE PACEMAKER," assigned to Cardiac Pacemakers, Inc., the disclosure of which is incorporated herein by reference in its entirety. It is understood, however, that the present invention also includes using a different number of electrodes (e.g., 2 or 3 electrodes, or more than 4 electrodes). In one example, a first conductor of multiconductor lead 110 electrically couples a first electrode, such as tip electrode 120 (e.g., disposed at the apex of the right ventricle of heart 115), to device 105. A second conductor of multiconductor lead 110 independently electrically couples a second electrode, such as ring electrode 125, to device 105. In one embodiment, device 105 includes a hermetically sealed housing 130, formed from a conductive metal, such as titanium. Housing 130 (also referred to as a "case" or "can") is substantially covered over its entire surface by a suitable insulator, such as silicone rubber, except for at a window that forms a third electrode, referred to as a "case" or "can" or "housing" electrode 135. In one embodiment, a header 140 is mounted on housing 130 for receiving lead 110. Header 140 is formed of an insulative material, such as molded plastic. In the illustrated embodiment, header 140 also includes at least one receptacle, such as for receiving lead 110 and electrically coupling conductors of lead 110 to device 105. Header 140 also includes a fourth electrode, referred to as indifferent electrode 145.

FIG. 1 also illustrates generally portions of device 105, together with schematic illustrations of connections to the various electrodes. Device 105 includes an electrical energy source serving as a test signal generator, such as exciter 150. Exciter 150 delivers an electrical test energy, such as a strobed sequence of current pulses or other test energy, to heart 115 (e.g., between ring electrode 125 and tip electrode 120, or using any other electrode configuration suitable for delivering the current pulses). In response to the excitation signal provided by exciter 150, a response signal is sensed by signal processor 155 (e.g., between tip electrode 120 and indifferent electrode 145, or using any other suitable electrode configuration). The electrical excitation signal is also referred to herein as a test signal or test stimulus because it serves as an active energy source from which a heart impedance is detected; however, it is understood that this signal need not, and typically does not, have the magnitude of energy required to excite or stimulate cardiac or other muscular tissue to contract. Instead, the excitation signal need only provide enough response for the signal processor to obtain useful information about heart impedance. Moreover, while the illustrated embodiment uses a current excitation stimulus to obtain a voltage response signal from which heart impedance can be determined, it is understood that a voltage excitation stimulus and current response signal could also be used to obtain heart impedance information. One example of using a high frequency carrier signal to provide a test stimulus and obtain a thoracic impedance response is discussed in Hartley et al. U.S. Pat. No. 6,076,015 ("the Hartley et al. patent") entitled "RATE ADAPTIVE CARDIAC RHYTHM MANAGEMENT DEVICE USING TRANSTHORACIC IMPEDANCE," assigned to Cardiac Pacemakers, Inc., the disclosure of which is incorporated herein by reference in its entirety.

In one embodiment, the response signal sensed by signal processor 155 is a voltage that, for the given test current, represents a thoracic impedance (i.e., a resistive or reactive impedance associated with at least a portion of a thorax of a living organism). This thoracic impedance signal is influenced by the patient's thoracic intravascular fluid tension, heart beat, and breathing (also referred to as "respiration" or "ventilation"). A "de" or "baseline" or "low frequency" component of the thoracic impedance signal (e.g., less than a cutoff value that is approximately between 0.1 Hz and 0.5 Hz, inclusive, such as, for example, a cutoff value of approximately 0.1 Hz) provides information about the subject patient's thoracic fluid tension, and is therefore influenced by intravascular fluid shifts to and away from the thorax. Higher frequency components of the thoracic impedance signal are influenced by the patient's breathing (e.g., approximately between 0.05 Hz and 2.0 Hz inclusive) and heartbeat (e.g., approximately between 0.5 Hz and 10 Hz inclusive).

As discussed above, a too-low intravascular fluid tension in the thorax ("thoracic hypotension") may result from changes in posture. This is sometimes referred to as orthostatic hypotension. For example, in a person who has been in a recumbent position for some time, approximately ⅓ of the blood volume is in the thorax. When that person then sits upright, approximately ⅓ of the blood that was in the thorax migrates to the lower body. This increases thoracic impedance. Approximately 90% of this fluid shift takes place within 2 to 3 minutes after the person sits upright.

Aside from such changes in posture, however, thoracic hypotension may also manifest itself as disautonomic syncope or vasovagal syncope, or other condition in which intravascular fluid shift from the thorax may or may not correspond directly to a change in the patient's posture. According to the present techniques, however, hypotension resulting from a fluid shift away from the thorax is indicated by an increase in the baseline thoracic impedance, regardless of whether the cause of the hypotension is orthostatic. In response to the detection of hypotension, system 100 provides a therapy, such as by increasing the patient's heart rate by delivering pacing stimuli to the heart more rapidly. Upon detecting thoracic hypotension, signal processor 155 outputs an indicated rate signal at node/bus 160 to controller 165. In one embodiment, based on the indicated rate signal at node 160, controller 165 adjusts the rate of delivery of cardiac rhythm management therapy, such as electrical pacing stimuli, to heart 115 by therapy circuit 170. Such pacing stimuli includes, for example, providing bipolar pacing between tip electrode 120 and ring electrode 125, providing unipolar pacing between can electrode 135 and either of tip electrode 120 or ring electrode 125, or providing pacing stimuli using any other suitable electrode configuration. By increasing pacing rate in this manner, system 100 effects a faster return of blood from the extremities to the thorax and head, thereby reducing or avoiding the symptoms of dizziness or fainting. By using thoracic impedance to directly measure thoracic intravascular fluid tension, rather than measuring a change of posture or other secondary variable, system 100 provides more reliable treatment of thoracic hypotension and its associated symptoms. However, it is understood that in one embodiment, system 100 bases its treatment of hypotension based not only on the thoracic impedance-based measurement of intravascular fluid tension, but also one or more of these secondary variables (e.g., also using an accelerometer to detect a change in posture).

In another embodiment, the indicated pacing rate is not based solely on the intravascular thoracic fluid tension information obtained from the thoracic impedance signal. In one such embodiment, for example, the indicated pacing rate is also based on the patient's intrinsic heart rate, such as obtained by sensing intrinsic heart depolarizations using sense amplifier 175. In other embodiments, the intravascular fluid tension information is used in combination with at least one other indication of the patient's metabolic need for an increased heart rate. This other indication of metabolic need is obtained either from the same thoracic impedance sensor technique discussed above (but using other thoracic impedance information such as, for example, breathing or heart rate) or from a completely different sensor. One example of such a different sensor is an accelerometer used to sense the patient's activity as a sensor-driven indicator of the need for a higher heart rate. An example of a "minute ventilation" technique of using the breathing information carried by the thoracic impedance signal as an indication of the patient's metabolic need for a higher heart rate is discussed in Hartley et al. U.S. Pat. No. 6,076,015 ("the Hartley et al. patent") entitled "RATE ADAPTIVE CARDIAC RHYTHM MANAGEMENT DEVICE USING TRANSTHORACIC IMPEDANCE," assigned to the assignee of the present invention, the disclosure of which is incorporated herein by reference in its entirety. The background portion of the Hartley et al. patent also discusses a number of other sensors and techniques for providing an indication of metabolic need for adjusting the heart rate; it is understood that such techniques, or any other technique known in the art, could be blended or otherwise used in combination with the techniques discussed herein for increasing heart rate in response to an increase in the baseline transthoracic impedance corresponding to intravascular fluid hypotension. The Hartley et al. patent also discusses in detail one technique for obtaining transthoracic impedance information using exciter 150, however, it is understood that the present invention is not limited to such technique, but could use any known technique for providing a test signal and sensing a resulting impedance.

Signal Processor

Figure 2:
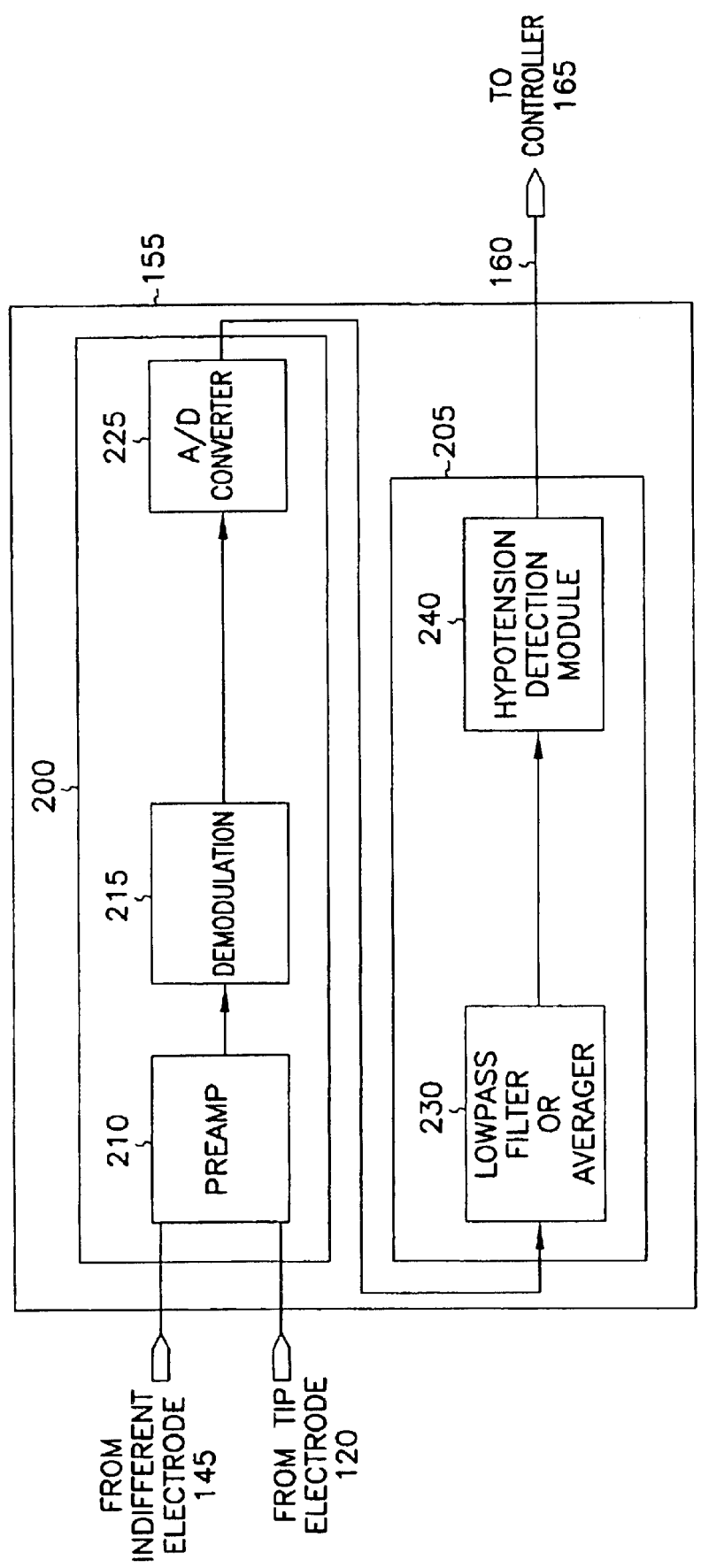
FIG. 2 is a block diagram illustrating generally one embodiment of portions of a signal processor associated with detecting hypotension based on thoracic impedance.

FIG. 2 is a block diagram illustrating generally, by way of example, but not by way of limitation, one embodiment of portions of signal processor 155. In this embodiment, signal processor 155 includes analog signal processing circuit 200 and digital signal processing circuit 205. Inputs of a preamplifier 210 (also referred to as a preamp or a receiver) of analog signal processing circuit 200 are electrically coupled to each of indifferent electrode 145 and tip electrode 120 for receiving a signal in response to the above-discussed stimuli provided by exciter 150. Analog signal processing circuit 200 also includes demodulator 215, receiving the output of preamplifier 210, and providing a demodulated output signal to analog-to-digital (A/D) converter 225. An output signal from A/D converter 225 is received at lowpass filter (or averager) 230 of digital signal processing circuit 205. The Hartley et al. patent discusses the structure and operation of one embodiment of preamp 210 and demodulator 215.

In one embodiment, digital signal processing circuit 205 is included within controller 165 such as, for example, as a sequence of instructions executed by a microprocessor. In another embodiment, digital signal processing circuit 205 includes separately implemented hardware portions dedicated to performing the digital signal processing tasks discussed below. Hypotension detection module 240 receives an output signal from the averager or other lowpass filter 230, and provides an indication of the hypotension at node 160 to controller 165, which controls the rate at which pacing stimuli pulses are issued by therapy circuit 170.

Figure 3:
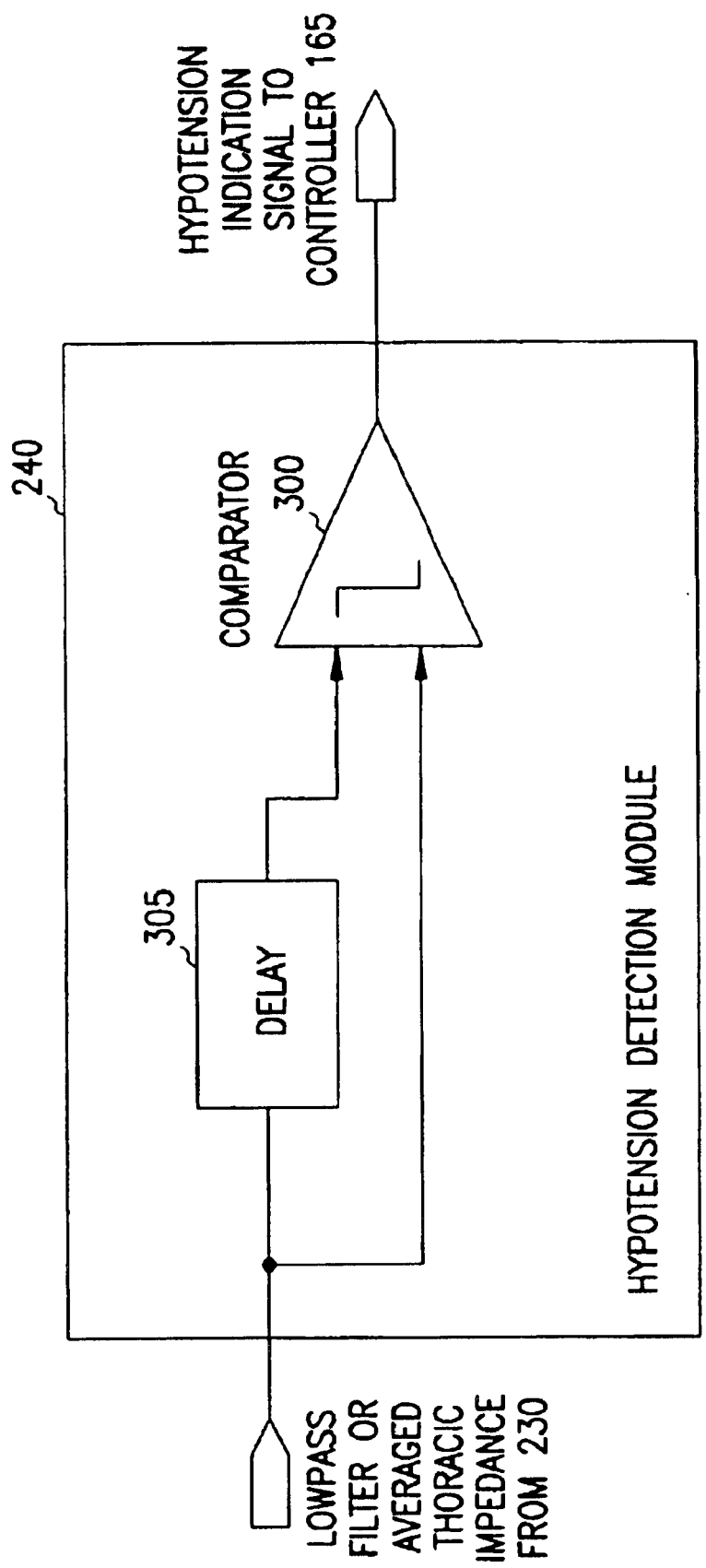
FIG. 3 is a schematic/block diagram illustrating generally, one embodiment of portions of a hypotension detection module.

FIG. 3 is a schematic/block diagram illustrating generally, by way of example, but not by way of limitation, one embodiment of portions of hypotension detection module 240. This embodiment provides a digital comparator 300 and a memory storage location, such as delay 305, for storing a previous baseline thoracic impedance received from lowpass filter or averager 230. In one embodiment, this delay is approximately between 3 and 120 seconds inclusive (e.g., 30 seconds). By comparing a difference between the present baseline thoracic impedance and its previous value to a threshold value, comparator 300 provides an output signal that indicates the presence of thoracic hypotension to controller 165. Comparator 300 includes embodiments both with and without hysteresis. In an alternative embodiment, comparator 300 is replaced by a difference circuit that provides, instead of a binary indication of thoracic hypotension, a multi-valued indication of the magnitude of the thoracic hypotension.

Figure 4:
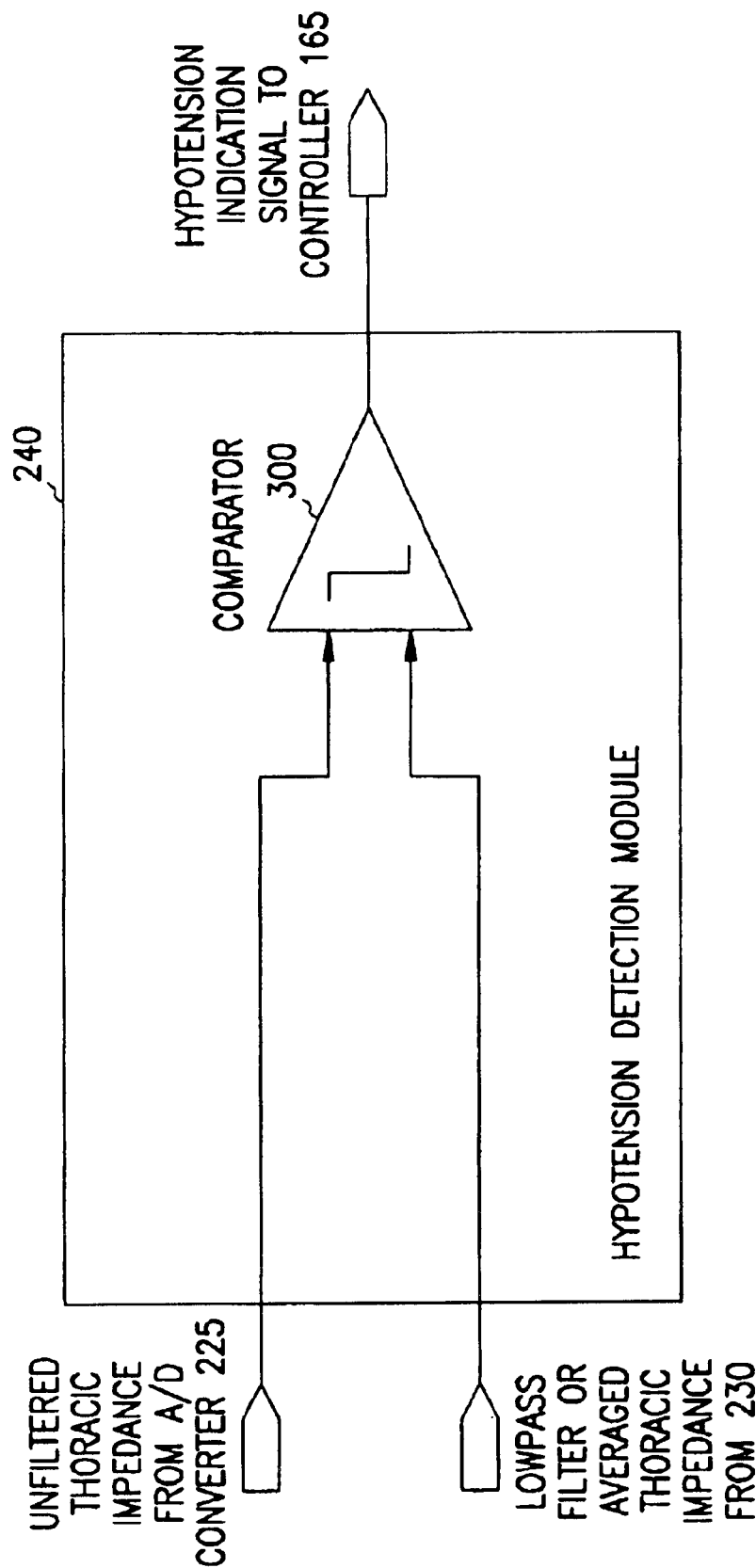
FIG. 4 is a schematic/block diagram illustrating generally, one embodiment of portions of a hypotension detection module.

FIG. 4 is a schematic/block diagram illustrating generally, by way of example, but not by way of limitation, another embodiment of portions of hypotension detection module 240. This embodiment includes a digital comparator 300 that receives the baseline thoracic impedance from lowpass filter or averager 230 as well as an unfiltered (or lesser filtered) "instantaneous" thoracic impedance from A/D converter 225. By comparing a difference between the present baseline impedance and the present "instantaneous" thoracic impedance to a threshold value, comparator 300 provides an output signal that indicates the presence of thoracic hypotension to controller 165. Comparator 300 includes embodiments both with and without hysteresis. In an alternative embodiment, comparator 300 is replaced by a difference circuit that provides, instead of a binary indication of thoracic hypotension, a multi-valued indication of the magnitude of the thoracic hypotension. It is understood that the embodiments of FIGS. 3 and 4 may be combined, for example, to base the indication of thoracic hypotension on both the unfiltered and lowpass filtered thoracic impedance signals.

In one embodiment, hypotension detection module 240 indicates the detection of thoracic hypotension based on an increase of approximately between 2 and 20 ohms inclusive (e.g., 6 ohms) in the received lowpass filtered thoracic impedance signal, which, in one embodiment, is averaged such as using a fixed or moving window average over a time period that is approximately between 5 seconds and 5 minutes inclusive (e.g., 1 minute). However, it is understood that lowpass filter 230 need not be an averager; other embodiments include a digital (or, if moved before A/D converter 225, analog) filter having an effective cutoff frequency (i.e., effective 3 dB attenuation point of a single or multiple pole filter) that passes a signal associated with thoracic fluid shift and attenuates a higher frequency signal such as that associated with the patient's breathing or heart beat.

In another embodiment, hypotension detection module 240 also receives a thoracic impedance signal from A/D converter 225, without being filtered or averaged (or alternatively, averaged over a shorter time period) by lowpass filter or averager 230. In this embodiment, hypotension detection module 240 uses this unfiltered thoracic impedance signal in combination with the averaged thoracic impedance signal, output by lowpass filter or averager 230, to indicate the detection of thoracic hypotension. In one example, where this "instantaneous" or "unfiltered" thoracic impedance exceeds the averaged thoracic impedance (also referred to as the "baseline," "low-frequency," or "dc" thoracic impedance) by a threshold amount that is approximately between 2 and 30 ohms inclusive, then an indication of thoracic hypotension is triggered. Hypotension detection module 240 provides an indication of detected hypotension, at node 160, to controller 165; this indication may be, among other things, a binary indication of whether hypotension is present or, alternatively, a signal that includes information about the degree of hypotension present (e.g., based on the change in baseline thoracic impedance and/or difference between the instantaneous and average thoracic impedance).

In response to the indication of thoracic hypotension received from hypotension detection module 240, controller 165 provides an appropriate therapy such as by adjusting the rate of delivery of pacing therapy to heart 115. In one embodiment, detection of hypotension triggers pacing at a particular rate programmed by the physician (e.g., 90, 100, 110, 120, 130 beats per minute) for a particular period of time (e.g., 30 seconds to 10 minutes), and then reverts back to the previous pacing rate before hypotension was detected, or to a different pacing rate if so indicated by one or more other sensors. For example, if the patient had a paced or intrinsic heart rate of 60 beats per minute when hypotension is detected, controller 165 then paces the patient at a hypotension treatment rate of 110 beats per minute, for example, to counter the hypotension. After the desired duration of this treatment, such as 2 minutes, for example, controller 165 returns to the previous rate of 60 beats per minute. If, for example, a minute ventilation, accelerometer, or other sensor indicates a metabolic need for a different rate, however (e.g., 70 beats per minute indicated by an accelerometer tracking patient activity) then controller 165 returns to that appropriately indicated rate (e.g., 70 beats per minute indicated by the accelerometer). In a further variation of this and other embodiments, the rate change to or from the hypotension treatment rate is not instantaneous, but incorporates a rate-smoothing algorithm such as is known in the art.

In another embodiment, controller 165 responds to a detection of hypotension by triggering an incremental increase (e.g., 10, 20, 30 . . . 50 beats per minute) in the pacing rate over the previous paced or intrinsic rate for a particular period of time (e.g., 30 seconds to 10 minutes), and then reverts back to that previous pacing rate or other suitable rate such if so determined by other direct or indirect sensors of metabolic need. For example, if hypotension is detected when a patient has a paced or intrinsic heart rate of 65 beats per minute, and an incremental increase of 30 beats per minute has previously been programmed, then controller 165 increases the pacing rate to 95 beats per minute for the programmed duration of this treatment, such as 5 minutes, for example, after which time it reverts back to 65 beats per minute unless a metabolic need sensor indicates that reversion to another rate is more appropriate. In a further embodiment, the incremental increase is itself a function of the intrinsic or sensor-indicated heart rate, so that a higher intrinsic or sensor-indicated rate results in a smaller (or larger) incremental change in pacing rate when hypotension is detected. In yet a further embodiment, the incremental rate increase is a function of the degree of detected hypotension. In such an example, a larger increase in baseline thoracic impedance is associated with a larger incremental rate increase for treating the hypotension.

Figure 5:
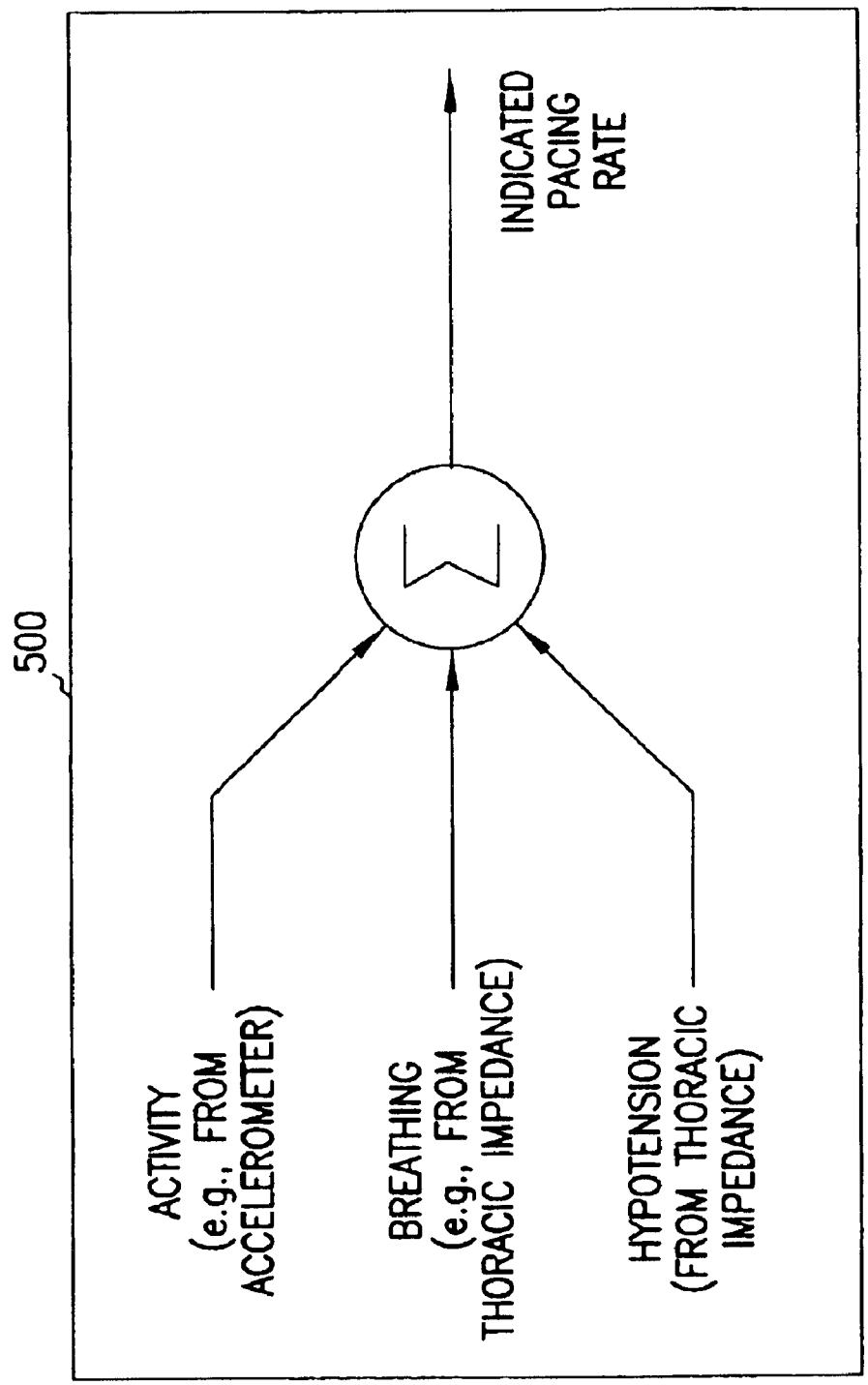
FIG. 5 is a block diagram illustrating generally one embodiment of portions of a blending module providing an indicated pacing rate based on activity, breathing, and/or a thoracic impedance-based measurement of hypotension.

In a further embodiment, hypotension detected based on thoracic impedance is one factor used in providing a blended indicated pacing rate; the indicated pacing rate is also based on at least one other factor such as the patient's breathing (e.g., using a minute ventilation technique) or activity (e.g., using an accelerometer technique). FIG. 5 is a block diagram illustrating generally, by way of example, not by way of limitation, one embodiment of a blending module 500 in controller 165 or elsewhere that provides an indicated pacing rate based on activity, breathing, and/or a thoracic impedance-based measurement of hypotension, each scaled appropriately to provide a desired response.

In yet another embodiment, controller 165 responds to a detection of hypotension by triggering the application of high voltage pacing or other increased electrical stimulation such as, for example, to increase the contractility of the heart. This therapy is carried out either in combination with or in lieu of a rate increase. In one example, a patient being paced using pulses of 2.0 Volts and 0.5 milliseconds is treated, upon detection of hypotension, by pacing pulses at a voltage level approximately between 5 Volts and 50 Volts inclusive,-a current level approximately between 5 milliamperes and 200 milliamperes inclusive, and/or a pulsewidth approximately between 10 milliseconds and 100 milliseconds inclusive for a suitable time period (e.g., 1 minute) before returning the therapy to previous energy levels.

In still another embodiment, controller 165 responds to the detection of hypotension by triggering the application of drug therapy from an implantable or external drug delivery system. Thus, the present system envisions a broad range of therapeutic responses to hypotension detected from thoracic impedance.

Other Electrode Configuration Examples

FIG. 1 illustrated an electrode configuration for measuring transthoracic impedance in which a test current was provided between a ring electrode 125 and a housing electrode 135, a resulting voltage is measured across tip electrode 120 and header electrode 145, and a transthoracic impedance is calculated based on the measured voltage and test current. However, other embodiments use different electrode configurations to determine transthoracic impedance, some examples of which are discussed below.

In a first embodiment of determining transthoracic impedance using the electrodes illustrated in FIG. 1, the test current is provided between the ring electrode 125 and one of housing electrode 135 or header electrode 145, and a resulting voltage is measured across tip electrode 120 and the other of housing electrode 135 or header electrode 145.

In a second embodiment, the test current is provided between tip electrode 120 and one of housing electrode 135 or header electrode 145, and the resulting voltage is measured between ring electrode 125 and the other of housing electrode 135 or header electrode 145.

In a third embodiment, the test current is provided between: (a) one of ring electrode 125 or tip electrode 120; and (b) one of housing electrode 135 or header electrode 145. A resulting voltage is measured across: (a) the same one of ring electrode 125 or tip electrode 120; and (b) and the other of housing electrode 135 or header electrode 145.

In a fourth embodiment, the test current is provided between: (a) one of housing electrode 135 or header electrode 145; and (b) one of tip electrode 120 or ring electrode 125. A resulting voltage is measured across: (a) the same one of housing electrode 135 or header electrode 145; and (b) the other one of tip electrode 120 or ring electrode 125.

Figure 6:
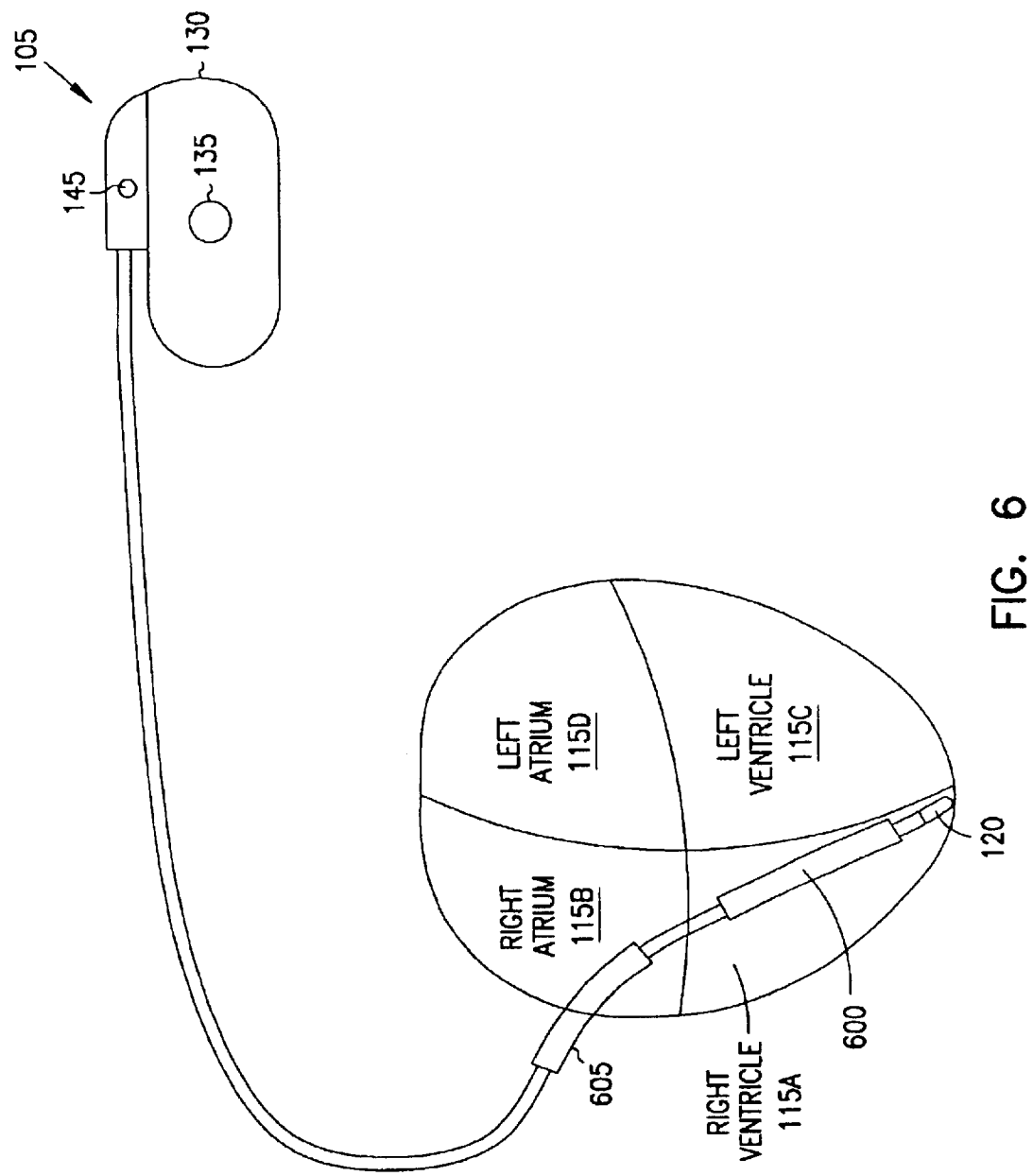
FIG. 6 is a schematic illustration of an alternate electrode arrangement including one or more defibrillation electrodes.

FIG. 6 illustrates generally a cardiac rhythm management device 105 and a lead that includes a tip electrode 120, a first coil or other defibrillation electrode 600 associated with a right ventricle 115A of heart 115, and a second coil or other defibrillation electrode 605 associated with a right atrium 115B of heart 115.

In a first embodiment of determining transthoracic impedance using the electrodes illustrated in FIG. 6, the test current is provided between the first defibrillation electrode 600 and one of housing electrode 135 or header electrode 145, and a resulting voltage is measured across tip electrode 120 and the other of housing electrode 135 or header electrode 145.

In a second embodiment, the test current is provided between tip electrode 120 and one of housing electrode 135 or header electrode 145, and the resulting voltage is measured between first defibrillation electrode 600 and the other of housing electrode 135 or header electrode 145.

In a third embodiment, the test current is provided between: (a) one of first defibrillation electrode 600 or tip electrode 120; and (b) one of housing electrode 135 or header electrode 145. A resulting voltage is measured across: (a) the same one of first defibrillation electrode 600 or tip electrode 120; and (b) and the other of housing electrode 135 or header electrode 145.

In a fourth embodiment, the test current is provided between: (a) one of housing electrode 135 or header electrode 145; and (b) one of tip electrode 120 or first defibrillation electrode 600. A resulting voltage is measured across: (a) the same one of housing electrode 135 or header electrode 145; and (b) the other one of tip electrode 120 or first defibrillation electrode 600.

In a fifth embodiment, the test current is provided between second defibrillation electrode 605 and one of housing electrode 135 or header electrode 145. A resulting voltage is measured across second defibrillation electrode 605 and the other of housing electrode 135 or header electrode 145.

Figure 7:
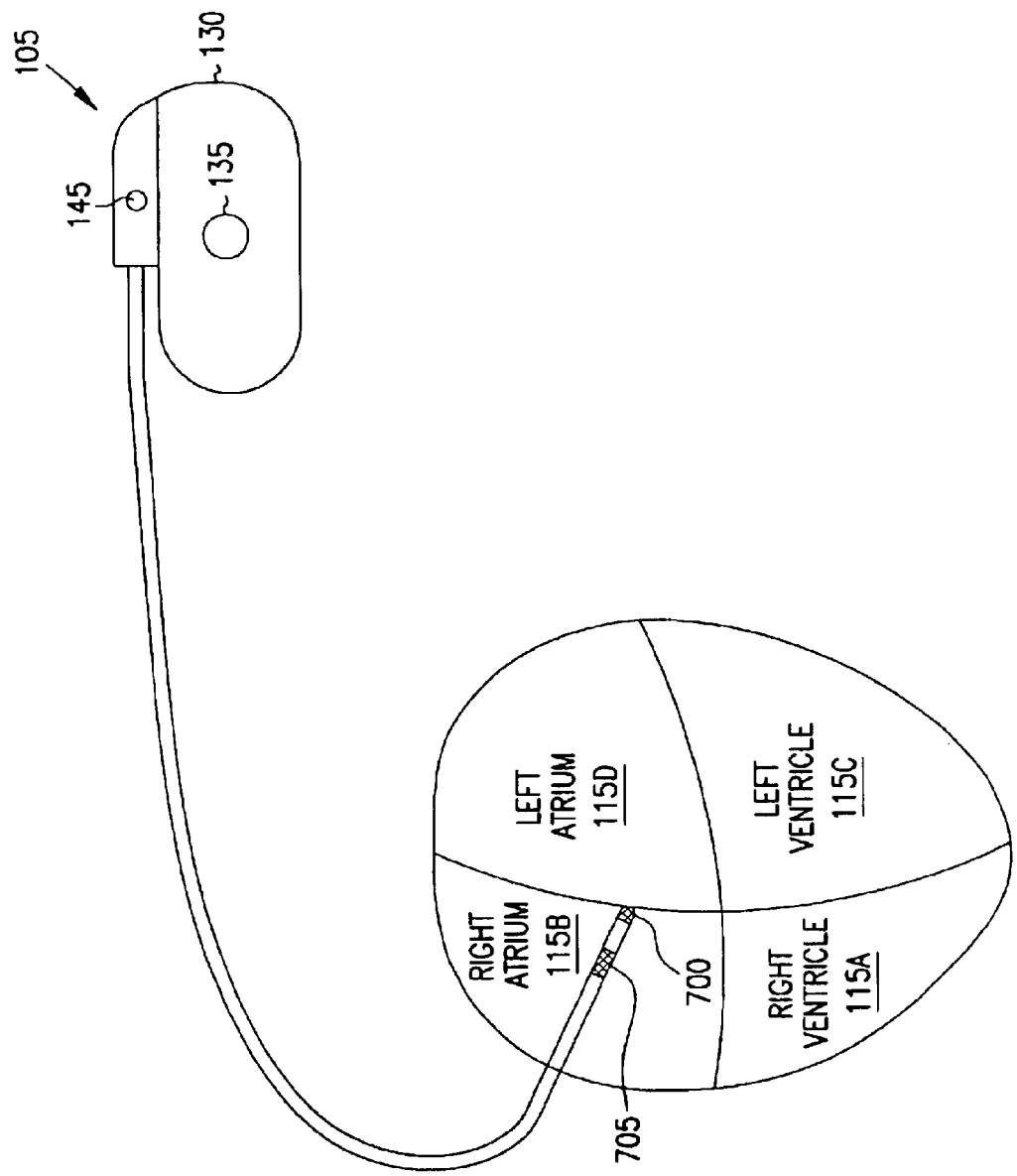
FIG. 7 is a schematic illustration of an alternate electrode arrangement including one or more atrial electrodes.

FIG. 7 illustrates generally a cardiac rhythm management device 105 and a lead that includes a tip electrode 700 and ring electrode 705 associated with a right atrium 115B of heart 115.

In a first embodiment of determining transthoracic impedance using the electrodes illustrated in FIG. 7, the test current is provided between the ring electrode 705 and one of housing electrode 135 or header electrode 145, and a resulting voltage is measured across tip electrode 700 and the other of housing electrode 135 or header electrode 145.

In a second embodiment, the test current is provided between tip electrode 700 and one of housing electrode 135 or header electrode 145, and the resulting voltage is measured between ring electrode 705 and the other of housing electrode 135 or header electrode 145.

In a third embodiment, the test current is provided between: (a) one of ring electrode 705 or tip electrode 700; and (b) one of housing electrode 135 or header electrode 145. A resulting voltage is measured across: (a) the same one of ring electrode 705 or tip electrode 700; and (b) and the other of housing electrode 135 or header electrode 145.

In a fourth embodiment, the test current is provided between: (a) one of housing electrode 135 or header electrode 145; and (b) one of tip electrode 700 or ring electrode 705. A resulting voltage is measured across: (a) the same one of housing electrode 135 or header electrode 145; and (b) the other one of tip electrode 700 or ring electrode 705.

Figure 8:
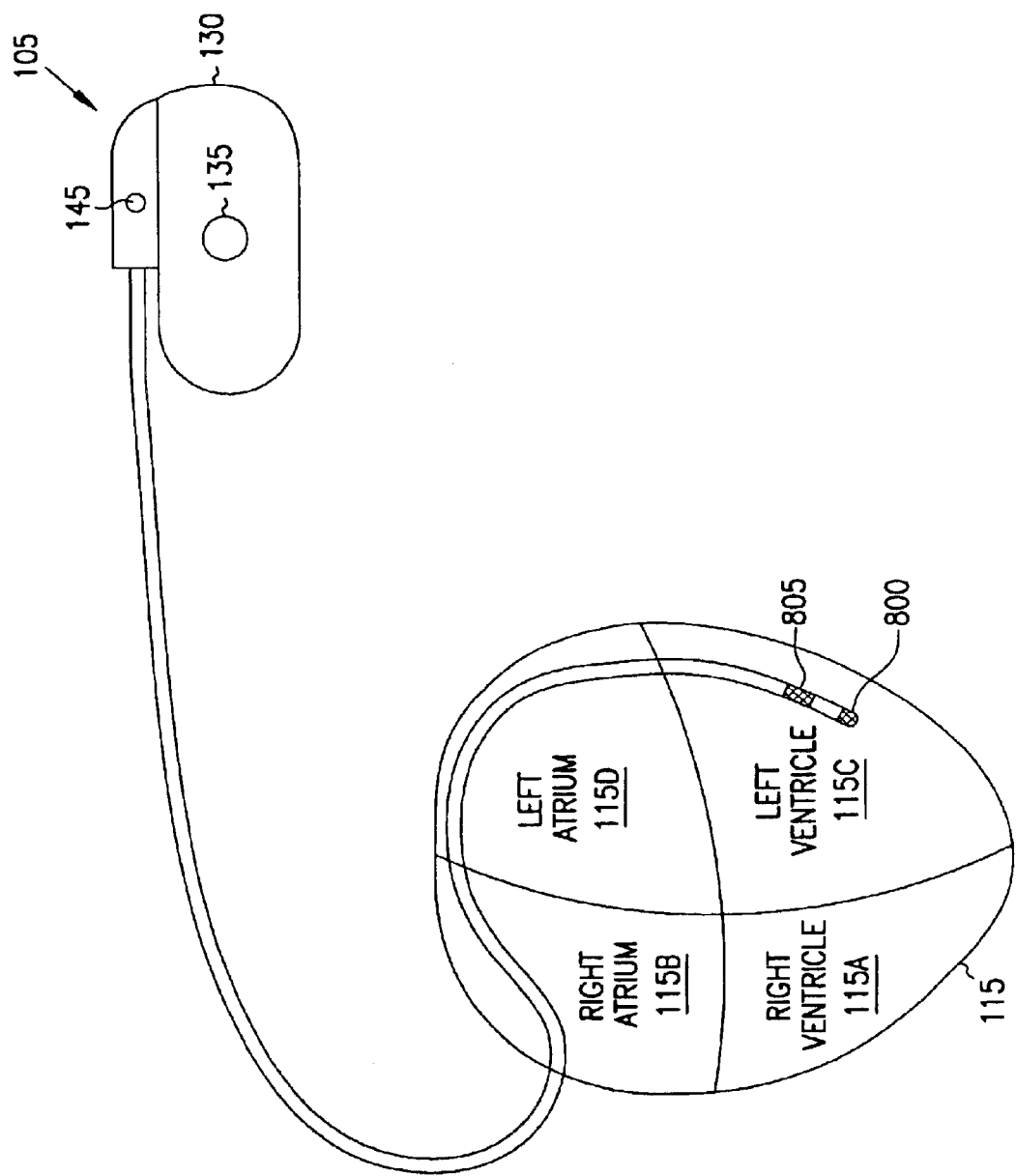
FIG. 8 is a schematic illustration of an alternate electrode arrangement including one or more left heart electrodes such as, for example, left ventricular electrodes.

FIG. 8 illustrates generally a cardiac rhythm management device 105 and a lead that includes a tip electrode 800 and ring electrode 805 associated with a left ventricle 115C of heart 115 by being introduced into a coronary sinus and/or great cardiac vein and/or one of its tributaries in the left ventricular free wall, or by being epicardially placed in proximity to left ventricle 115C.

In a first embodiment of determining transthoracic impedance using the electrodes illustrated in FIG. 8, the test current is provided between the ring electrode 805 and one of housing electrode 135 or header electrode 145, and a resulting voltage is measured across tip electrode 800 and the other of housing electrode 135 or header electrode 145.

In a second embodiment, the test current is provided between tip electrode 800 and one of housing electrode 135 or header electrode 145, and the resulting voltage is measured between ring electrode 805 and the other of housing electrode 135 or header electrode 145.

In a third embodiment, the test current is provided between: (a) one of ring electrode 805 or tip electrode 800; and (b) one of housing electrode 135 or header electrode 145. A resulting voltage is measured across: (a) the same one of ring electrode 805 or tip electrode 800; and (b) and the other of housing electrode 135 or header electrode 145.

In a fourth embodiment, the test current is provided between: (a) one of housing electrode 135 or header electrode 145; and (b) one of tip electrode 800 or ring electrode 805. A resulting voltage is measured across: (a) the same one of housing electrode 135 or header electrode 145; and (b) the other one of tip electrode 800 or ring electrode 805.

Figure 9:
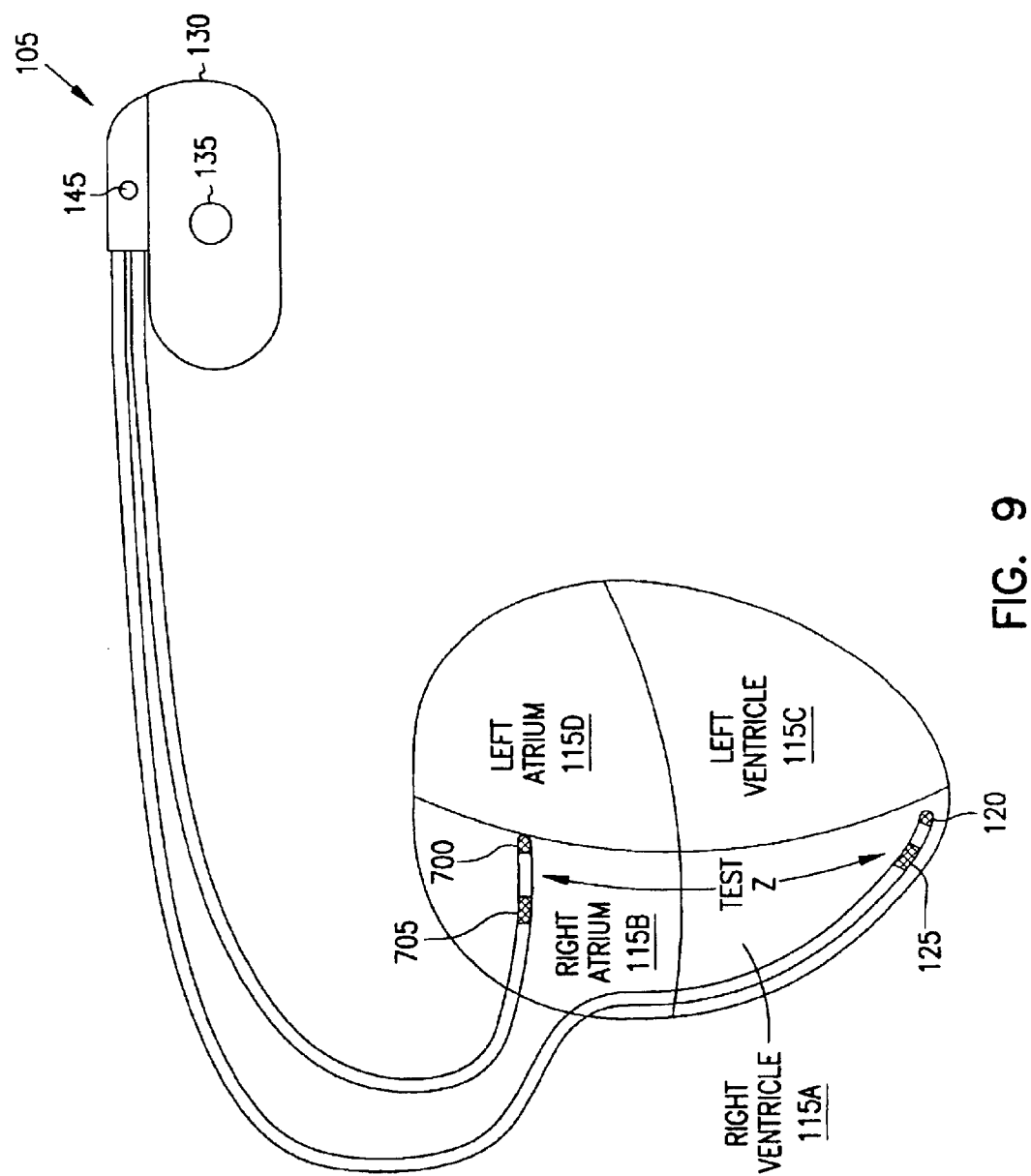
FIG. 9 is a schematic illustration of an alternate electrode arrangement for measuring a component of thoracic impedance between atrial electrodes and ventricular electrodes.
Figure 10:
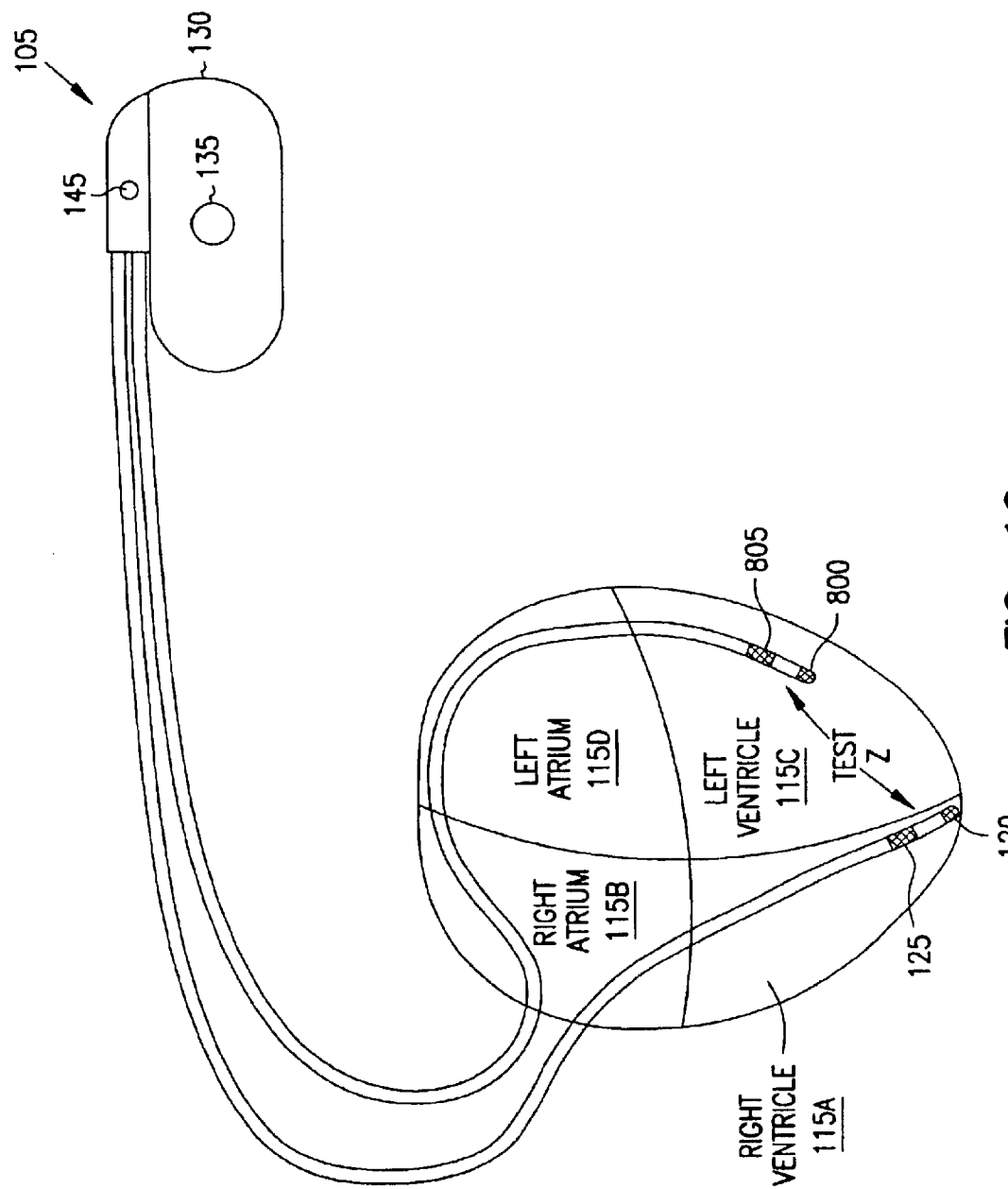
FIG. 10 is a schematic illustration of an alternate electrode arrangement for measuring a component of thoracic impedance between right heart (e.g., right ventricular) and left heart (e.g., left ventricular) electrodes.

FIGS. 1 and 6–8 illustrate, among other things, configurations in which one or more electrodes is located inside of, or in close proximity to, heart 115, and one or more electrodes is located at a distance away from heart 115, such as, for example, on pectorally or abdominally implanted device 105. This distance provides an effective portion of the thorax for which the transthoracic impedance is sampled. However, a lesser distance may also be used for sampling thoracic impedance, in fact, thoracic impedance may be sampled using electrodes in more close proximity, such as an embodiment in which all electrodes are associated with heart 115, as illustrated in the examples of FIGS. 9 and 10.

Some of the embodiments discussed above (e.g., that of FIG. 1) use four electrodes for measuring impedance. In such a technique for measuring impedance, both electrodes used for sensing the voltage are different than both of the electrodes used for delivering the test current, so that the impedance of the leads coupling the test current source to the test current electrodes does not affect the voltage measurement. However, this is not a requirement. A three electrode arrangement (in which only one of the voltage sensing electrodes is different from the test current electrode pair) or even a two electrode arrangement (using the same electrodes for both delivering the test current and measuring the test voltage) may be used, although such arrangements may result in a larger steady-state (i.e., offset) component of the measured impedance due to the measurement apparatus and unrelated to the steady-state thoracic tissue impedance.

Conclusion

The above-discussed system provides, among other things, a cardiac rhythm management system using thoracic impedance measurements to detect and treat hypotension. It detects and treats hypotension that results either from a change in posture or is independent of any change in posture. It is to be understood that the above description is intended to be illustrative, and not restrictive. For example, the above-discussed embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." The term "lowpass filter" is understood to include, among other things, any averager, and use of the term "averager/lowpass filter" is used simply to emphasize that an averager is included in the term "lowpass filter."

What is claimed is:

1. A method including:

detecting a thoracic impedance signal associated with a portion of a subject's thorax; and providing a therapy to the subject's heart at least in part in response to a baseline portion of the detected thoracic impedance below about 0.5 Hz indicating a fluid shift away from the thorax, the therapy assisting to shift fluid back toward the thorax.

2. The method of claim 1, further including attenuating a high frequency component of the thoracic impedance signal.

3. A method including:
  detecting a thoracic impedance signal associated with a portion of a subject's thorax; and
  providing a therapy to the subject's heart at least in part in response to the detected thoracic impedance, including increasing a rate of pacing stimuli at least in part in response to an increase in the baseline portion of the thoracic impedance below about 0.5 Hz indicating a fluid shift away from the thorax, the therapy assisting to shift fluid back toward the thorax.

4. The method of claim 1, further including detecting a motion of the subject and providing the therapy to the subject's heart based at least in part on the detected motion of the subject.

5. The method of claim 1, further including detecting a breathing of the subject and providing the therapy to the subject's heart based at least in part on the detected breathing.

6. The method of claim 5, in which providing the therapy to the subject's heart includes adjusting a rate of delivery of pacing stimuli based on frequency components of the thoracic impedance associated with fluid shift away from the thorax and associated with the subject's breathing.

7. The method of claim 1, in which providing the therapy to the subject's heart includes providing a therapy from the group consisting essentially of:
  (a) increasing the subject's heart rate to a predetermined fixed value in response to an increase in detected thoracic impedance at a frequency associated with a fluid shift away from the thorax;
  (b) increasing the subject's heart rate by a predetermined fixed value in response to an increase in detected thoracic impedance at a frequency associated with a fluid shift away from the thorax;
  (c) adjusting an applied energy for modifying a heart rate or contractility in response to an increase in detected thoracic impedance at a frequency associated with a fluid shift away from the thorax; and
  (d) providing a drug to the subject in response to an increase in detected thoracic impedance at a frequency associated with fluid shift away from the thorax.

8. A method including:
  detecting a change in a thoracic impedance signal associated with a subject's thorax and including a thoracic fluid shift signal having a frequency component that is less than or equal to a cutoff frequency value that is between 0.01 Hz and 0.5 Hz inclusive; and
  increasing a rate of delivery of pacing stimuli at least in part in response to a detected increase in a baseline portion of the thoracic impedance signal indicating a fluid shift away from the thorax, the therapy assisting to shift fluid back toward the thorax and thereby decreasing the baseline portion of the thoracic impedance signal.

9. The method of claim 8, in which the cutoff frequency value is approximately 0.1 Hz.

10. The method of claim 8, further including detecting a motion of the subject and in which increasing the rate of delivery of pacing stimuli includes also basing the increase on the detected motion of the subject.

11. The method of claim 8, in which increasing the rate of delivery of pacing stimuli includes also basing the increase on a frequency component of the thoracic impedance associated with the subject's breathing.

12. A method including:
  detecting, using an implantable medical device to indicate thoracic hypotension resulting from a fluid shift away from the thorax using transthoracic impedance below about 0.5 Hz to indicate how much fluid is present in a thorax, both a hypotension associated with a change in a subject's posture and a hypotension that is not associated with a change in the subject's posture; and
  providing a therapy to the subject's heart at least in part in response to the detected hypotension, the therapy assisting to shift fluid back toward the thorax to reduce the hypotension.

13. The method of claim 12, in which providing the therapy includes increasing a heart rate in response to the detected hypotension.

14. A cardiac rhythm management system, including:
  first and second electrodes configured for association with a portion of a subject's thorax;
  a thoracic signal detection module, coupled to the first and second electrodes for receiving a thoracic impedance signal and including an averager/lowpass filter that obtains a baseline portion of the thoracic impedance signal below about 0.5 Hz that is associated with a fluid shift away from the thorax; and
  means for performing a function of providing therapy to the subject's heart based on the baseline portion of the thoracic impedance signal, the therapy assisting to shift fluid back toward the thorax.

15. A cardiac rhythm management system, including:
  first and second electrodes configured for association with a portion of a subject's thorax;
  a thoracic signal detection module, coupled to the first and second electrodes for receiving a thoracic impedance signal and including an averager/lowpass filter that obtains a baseline portion of the thoracic impedance signal below about 0.5 Hz that is associated with a fluid shift away from the thorax; and
  a pacing therapy output circuit providing therapy to the subject's heart in response to the baseline portion of the thoracic impedance signal indicating a fluid shift away from the thorax, the therapy assisting to shift fluid back toward the thorax.

16. A cardiac rhythm management system, including:
  first and second electrodes configured for association with a portion of a subject's thorax;
  means, coupled to the first and second electrodes for receiving a thoracic impedance signal, for performing the function of obtaining a baseline portion of the thoracic impedance signal below about 0.5 Hz that is associated with a fluid shift away from the thorax; and
  a pacing therapy output circuit providing therapy to the subject's heart in response to the baseline portion of the thoracic impedance signal indicating a fluid shift away from the thorax, the therapy assisting to shift fluid back toward the thorax.

17. A cardiac rhythm management system, including:
  first and second electrodes configured for association with a portion of a subject's thorax;
  a thoracic signal detection module, coupled to the first and second electrodes;
  third and fourth electrodes configured for association with a portion of a subject's heart;
  a pacing therapy output module, coupled to the third and fourth electrodes; and
  a pacing stimuli rate controller, coupled to the thoracic signal detection module for receiving a thoracic impedance signal including a baseline signal component associated with a fluid shift away from the thorax, the controller also coupled to the pacing therapy output module for adjusting the rate of delivery of pacing stimuli at least in part in response to the portion of the thoracic impedance signal below about 0.5 Hz associated with the thoracic fluid shift away from the thorax, the adjusting the rate of delivery of pacing stimuli assisting to shift fluid back toward the thorax.

18. The system of claim 17, in which at least one of the third and fourth electrodes is the same electrode as one of the first and second electrodes.

19. The system of claim 17, further including a thoracic test signal generator configured for association with the thorax for providing energy to the thorax for detecting thoracic impedance.

20. The system of claim 17, in which the rate controller further includes a lowpass filter coupled to the thoracic signal detection module.

21. The system of claim 20, in which the lowpass filter obtains the baseline portion of the thoracic impedance signal that is associated with a fluid shift away from the heart.

22. The system of claim 21, in which the lowpass filter attenuates a breathing portion of the thoracic impedance signal.

23. The system of claim 21, in which the lowpass filter attenuates a cardiac stroke portion of the thoracic impedance signal.

24. The system of claim 20, in which the lowpass filter attenuates a component of the thoracic impedance not associated with the thoracic fluid shift.

25. The system of claim 20, in which the lowpass filter includes an effective cutoff frequency that is between 0.01 Hz and 0.5 Hz.

26. The system of claim 25, in which the lowpass filter includes a cutoff frequency that is approximately equal to 0.1 Hz.

27. The system of claim 17, in which the controller includes a blending module for adjusting the rate of delivering pacing stimuli based on thoracic fluid shift and at least one of:
   (a) a breathing by the subject; and
   (b) a motion of the subject.

28. A cardiac rhythm management system, including:
   first and second electrodes configured for association with a portion of a subject's thorax;
   a thoracic signal detection module, coupled to the first and second electrodes;
   thoracic test signal generator configured for association with the thorax for providing energy to the thorax for detecting thoracic impedance;
   third and fourth electrodes configured for association with a portion of a subject's heart;
   a pacing therapy output module, coupled to the third and fourth electrodes; and
   a pacing stimuli rate control module, coupled to the thoracic signal detection module for receiving a thoracic impedance signal, the rate control module including a lowpass filter for distinguishing a baseline thoracic fluid shift signal below about 0.5 Hz from another variation in thoracic impedance, the rate control module also coupled to the pacing therapy output module for adjusting the rate of delivery of pacing stimuli at least in part in response to the thoracic fluid shift signal indicating a fluid shift away from the thorax, the adjusting the rate of delivery of pacing stimuli assisting to shift fluid back toward the thorax.

29. A cardiac rhythm management system, including:
   means for detecting a thoracic impedance;
   first and second electrodes, configured for association with a portion of a subject's heart;
   a pacing therapy output module, coupled to the first and second electrodes; and
   a pacing stimuli rate control module, coupled to the means for detecting thoracic impedance and the pacing therapy output module, the rate control module adjusting a rate of delivery of pacing stimuli at least in part in response to a baseline portion of the thoracic impedance below about 0.5 Hz indicating a thoracic fluid shift away from the thorax, the adjusting the rate of delivery of pacing stimuli assisting to shift fluid back toward the thorax.

30. The method of claim 3, further including attenuating a high frequency component of the thoracic impedance signal.

31. The method of claim 3, further including detecting a motion of the subject and providing the therapy to the subject's heart based at least in part on the detected motion of the subject.

32. The method of claim 3, further including detecting a breathing of the subject and providing the therapy to the subject's heart based at least in part on the detected breathing.

33. The method of claim 32, in which providing the therapy to the subject's heart includes adjusting a rate of delivery of pacing stimuli based on frequency components of the thoracic impedance associated with fluid shift away from the thorax and associated with the subject's breathing.

34. The method of claim 3, in which providing the therapy to the subject's heart includes providing a therapy from the group consisting essentially of:
   (a) increasing the subject's heart rate to a predetermined fixed value in response to an increase in detected thoracic impedance at a frequency associated with a fluid shift away from the thorax;
   (b) increasing the subject's heart rate by a predetermined fixed value in response to an increase in detected thoracic impedance at a frequency associated with a fluid shift away from the thorax;
   (c) adjusting an applied energy for modifying a heart rate or contractility in response to an increase in detected thoracic impedance at a frequency associated with a fluid shift away from the thorax; and
   (d) providing a drug to the subject in response to an increase in detected thoracic impedance at a frequency associated with fluid shift away from the thorax.

* * * * *